United States Patent [19]
Higashii et al.

[11] Patent Number: 5,779,934
[45] Date of Patent: Jul. 14, 1998

[54] FLUORINE-CONTAINING OPTICALLY ACTIVE COMPOUND, PROCESS FOR PREPARING THE SAME AND LIQUID CRYSTAL MIXTURE AND LIQUID CRYSTAL ELEMENT COMPRISING THE SAME

[75] Inventors: Takayuki Higashii, Irvington, N.Y.; Yukari Fujimoto, Takatsuki, Japan; Tsutomu Matsumoto, Kyoto, Japan; Masayoshi Minai, Moriyama, Japan; Chizu Sekine, Tsukuba, Japan; Kyoko Endo, Ibaraki, Japan; Koichi Fujisawa, Tsukuba, Japan

[73] Assignee: Sumitomo Chemical Company, Limited, Osaka, Japan

[21] Appl. No.: 388,424

[22] Filed: Feb. 14, 1995

[30] Foreign Application Priority Data

Feb. 14, 1994 [JP] Japan ................... 6-017413

[51] Int. Cl.[6] .................. C09K 19/34; C07D 239/00
[52] U.S. Cl. ................. 252/299.61; 252/299.62; 252/299.66; 544/242; 544/245; 544/249; 544/253; 544/295; 544/296; 544/298
[58] Field of Search ............ 252/299.61, 299.62, 252/299.66; 544/242, 245, 249, 253, 295, 296, 298

[56] References Cited

U.S. PATENT DOCUMENTS

| | | | |
|---|---|---|---|
| 4,709,030 | 11/1987 | Petrzilka et al. | 252/299.61 |
| 4,963,288 | 10/1990 | Saito et al. | 252/299.61 |
| 5,167,859 | 12/1992 | Wachtler et al. | 252/299.61 |
| 5,238,602 | 8/1993 | Petrzilka et al. | 252/299.61 |
| 5,240,637 | 8/1993 | Shinjo et al. | 252/299.61 |
| 5,275,756 | 1/1994 | Yamaguchi et al. | 252/299.61 |
| 5,393,459 | 2/1995 | Wachtler et al. | 252/299.61 |

FOREIGN PATENT DOCUMENTS

| | | |
|---|---|---|
| 0 440134 | 8/1991 | European Pat. Off. |
| 0 611119 | 2/1994 | European Pat. Off. |
| 0 636673 | 2/1995 | European Pat. Off. |
| 4 308028 | 9/1994 | Germany |
| 1 272571 | 10/1989 | Japan |
| 2-69467 | 3/1990 | Japan |

OTHER PUBLICATIONS

Kusumoto et al. (1993) *Chemistry Letters*, The Chemical Society of Japan pp. 1243–1246.
Hiyama et al. (5.10.18) Tokyo Institute of Technology, pp. 26–28.

*Primary Examiner*—Randy Gulakowski
*Attorney, Agent, or Firm*—Birch, Stewart, Kolasch & Birch, LLP

[57] ABSTRACT

A fluorine-containing optically active compound represented by the formula (1):

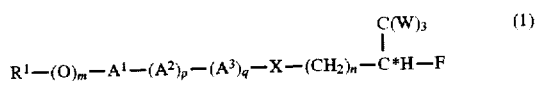

wherein $R_1$ is a saturated or unsaturated $C_3$–$C_{20}$ alkyl group or a saturated or unsaturated $C_3$–$C_{20}$ alkoxyalkyl group; $A^1$, $A^2$ and $A^3$ independently represent one of the following groups:

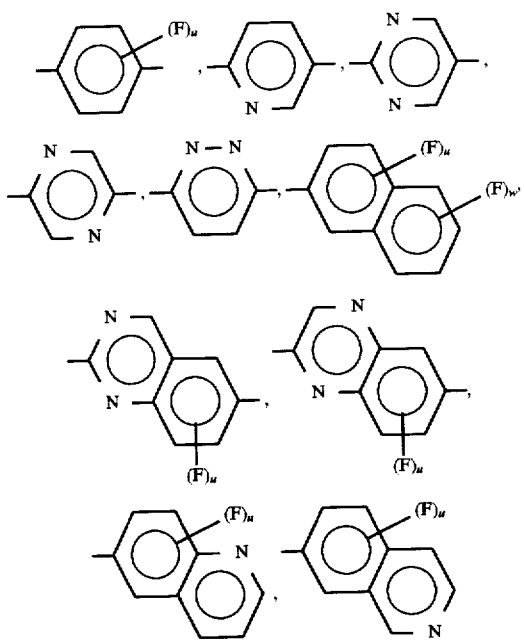

provided that, when $A^1$ is a condensed ring group, a sum of p and q is 0 or 1 and $A^2$ and $A^3$ are both monocyclic groups, or when $A^1$ is a monocyclic group, a sum of p and q is 1 or 2 with the proviso that when the sum of p and q is 2, $A^2$ and $A^3$ are both monocyclic groups; X is —$CH_2CH_2$—, —CH=CH— or —C≡C—; W is a fluorine atom or a hydrogen atom; n is an integer of 1 to 10; m, p and q are each 0 or 1; u and w are each an integer of 0 to 3; and * indicates an asymmetric carbon atom, which is useful as a component of a liquid crystal mixture.

15 Claims, No Drawings

FLUORINE-CONTAINING OPTICALLY ACTIVE COMPOUND, PROCESS FOR PREPARING THE SAME AND LIQUID CRYSTAL MIXTURE AND LIQUID CRYSTAL ELEMENT COMPRISING THE SAME

BACKGROUND OF THE INVENTION

1. Field of the Invention

The present invention relates to a fluorine-containing optically active compound, a process for preparing the same, and a liquid crystal mixture and a liquid crystal element comprising the same. In particular, the present invention relates to a fluorine containing optically active compound useful as a liquid crystal, a process for preparing the same, and a liquid crystal mixture and liquid crystal element comprising the same.

2. Description of the Related Art

In these days, as a liquid crystal display, a twisted nematic (TN) liquid crystal display is most widely used. A TN liquid crystal display has various advantages such as a low driving voltage, a low power demand, and the like. However, its response speed is slower than a light-emitting type display element such as a cathode ray tube display, an electroluminescence display, a plasma display, etc.

A new twisted nematic (namely, super twisted nematic, STN) liquid crystal display having an increased twist angle from 180° to 270° has been developed, but its response speed is still insufficient.

Though various improvements have been made in the liquid crystal displays, no TN liquid crystal display having a high response speed has been developed.

In a new display using a ferroelectric liquid crystal which is recently vigorously studied, a response speed may be expected to be increased greatly (see Clark et al. Appl. Phys. Lett., 36, 899 (1980)). This type of display makes use of a chiral smectic phase such as a chiral smectic C phase (hereinafter referred to as a "Sc* phase") which has a ferroelectric property. As phases having the ferroelectric property, there are known chiral smectic F, G, H and I phases in addition to the Sc* phase.

The ferroelectric liquid crystal material which is practically used in a ferroelectric liquid crystal element is required to have various characteristics. But, at present, a single compound cannot satisfy all the characteristics, and it is necessary to formulate a ferroelectric liquid crystal mixture comprising plural liquid crystal compounds, or at least one liquid crystal compound and at least one non-liquid crystal compound.

In addition to the ferroelectric liquid crystal mixture consisting of the ferroelectric liquid crystal compounds, Japanese Patent KOKAI Publication No. 195187/1986 discloses the preparation of a ferroelectric liquid crystal mixture by mixing a compound having a nonchiral smectic C, F, G, H or I phase (hereinafter referred to as "Sc-like phase") or a mixture containing such compound with at least one compound having the ferroelectric phase to make the liquid crystal mixture ferroelectric as a whole.

Mol. Cryst. Liq. Cryst., 89, 327 (1982) provides a ferroelectric liquid crystal mixture comprising a compound or a mixture having the Sc-like phase and at least one compound which is optically active but has no ferroelectric phase.

From the above, it is understood that a ferroelectric liquid crystal mixture can be formulated from at least one optically active compound which may have the ferroelectric phase or not, as a base compound. Preferably, the optically active compound has a liquid crystal phase. When it has no liquid crystal phase, it is preferred that its structure is similar to a liquid crystal compound, namely it is a quasi-liquid crystal compound.

However, there has been found no liquid crystal substance which has spontaneous polarization required for the high speed response and a low viscosity and exhibits the ferroelectric phase in a wide temperature range including room temperature.

Then, it is required to develop a liquid crystal having a novel structure with the increase of the applications of the liquid crystal.

SUMMARY OF THE INVENTION

An object of the present invention is to provide a novel fluorine-containing optically active compound useful as a ferroelectric liquid crystal material which has a spontaneous polarization and a high response speed and shows a ferroelectric liquid crystal phase in a temperature range around room temperature, or as a component of a ferroelectric liquid crystal mixture having such properties.

Another object of the present invention is to provide a process for preparing the novel fluorine-containing optically active compound of the present invention.

A further object of the present invention is to provide a liquid crystal mixture comprising the novel fluorine-containing optically active compound of the present invention.

A yet further object of the present invention is to provide a liquid crystal element comprising the novel fluorine-containing optically active compound of the present invention.

According to a first aspect of the present invention, there is provided a fluorine-containing optically active compound represented by the formula (1):

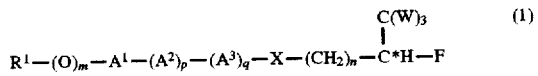

wherein $R^1$ is a saturated or unsaturated $C_3$–$C_{20}$ alkyl group or a saturated or unsaturated $C_3$–$C_{20}$ alkoxyalkyl group; $A^1$, $A^2$ and $A^3$ independently represent one of the following groups:

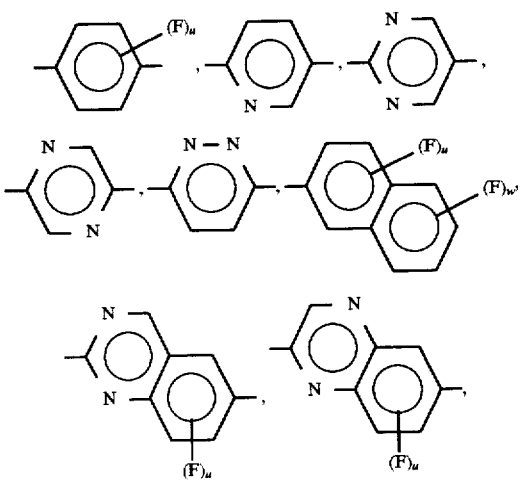

-continued

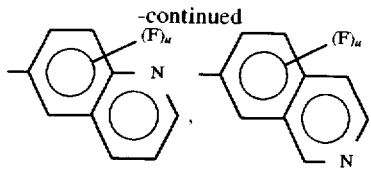

provided that, when $A^1$ is a condensed ring group, a sum of p and q is 0 or 1 and $A^2$ and $A^3$ are both monocyclic groups, or when $A^1$ is a monocyclic group, a sum of p and q is 1 or 2 with the proviso that when the sum of p and q is 2, $A^2$ and $A^3$ are both monocyclic groups; X is —CH$_2$CH$_2$—, —CH=CH— or —C—C≡C—; W is a fluorine atom or a hydrogen atom; n is an integer of 1 to 10; m, p and q are each 0 or 1; u and w are each an integer of 0 to 3; and * indicates an asymmetric carbon atom.

Herein, the condensed ring group is

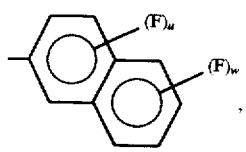

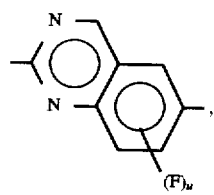

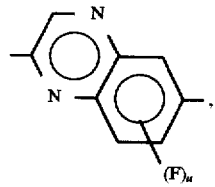

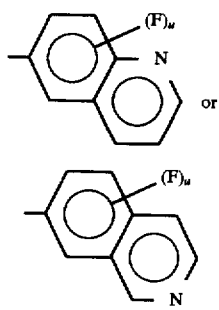

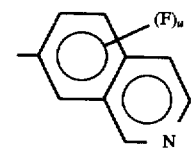

and the monocyclic group is

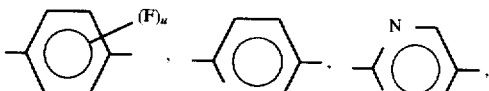

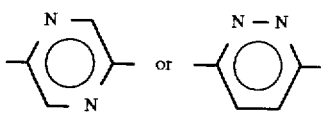

According to a second aspect of the present invention, there is provided a process for preparing a compound of the above formula (1) comprising fluorinating an alcohol derivative of the formula:

$$R^1-(O)_m-A^1-(A^2)_p-(A^3)_q-X-(CH_2)_n-\overset{C(W)_3}{\underset{|}{C^*H}}-OH \quad (2)$$

wherein $R^1$, $A^1$, $A^2$, $A^3$, X, W, m, n, p and q are the same as defined above, with a fluorinating agent.

According a third aspect of the present invention, there is provided a liquid crystal mixture comprising the fluorine-containing optically active compound of the formula (1).

According to a fourth aspect of the present invention, there is provided a liquid crystal display element comprising the fluorine-containing optically active compound of the formula (1).

DETAILED DESCRIPTION OF THE INVENTION

The compound of the formula (1) according to the present invention may be prepared by fluorinating an alcohol derivative of the formula (2) with a fluorinating agent.

The alcohol derivative (2) as a starting compound may be prepared by a per se conventional method, which can be represented by the following reaction formula:

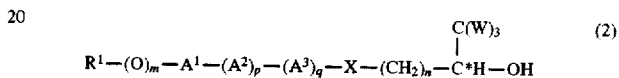

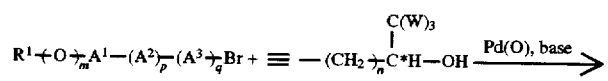

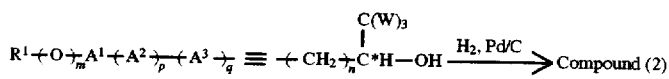

or

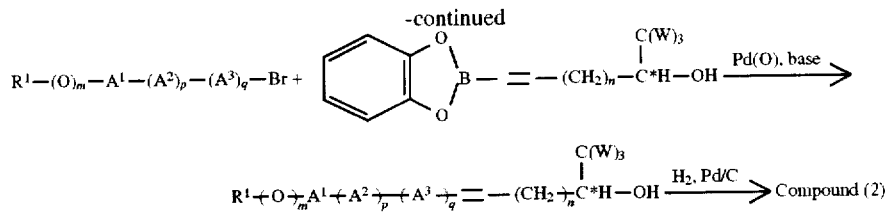

Preferred examples of the fluorinating agent to be used in the process of the present invention are hydrogen fluoride, its complex compounds, sulfur fluorides, fluoroolefins, and the like. Specific examples of the fluorinating agent are hydrogen fluoride-pyridine, hydrogen fluoride-triethylamine, sulfur tetrafluoride, diethylamino-sulfur trifluoride (DAST), morpholinosulfur trifluoride (morph-DAST), 2-chloro-1,1,2-trifluoroethylene, hexafluoropropene, and the like. They may be used independently or as a mixture of two or more of them. Further, they may be used in combination with diethylamine, diisopropylamine, morpholine, and so on.

In the fluorination reaction, an amount of the fluorinating agent is from 1.0 to 5 times equivalent, preferably from 1.0 to 2 times equivalent based on the amount of the alcohol derivative (2).

The fluorination reaction is usually carried out in the presence of a solvent such as a halohydrocarbon or a hydrocarbon. Specific examples of such solvent are hexane, benzene, toluene, dichloromethane, dichloroethane, chlorobenzene, and mixtures thereof. An amount of the solvent is not limited.

A fluorination reaction temperature is usually from −70° to +100° C., preferably from −70° to +50° C.

After fluorination, the compound (1) of the present invention can be isolated from a reaction mixture by any of conventional methods such as extraction, distillation, recrystallization or column chromatography.

In an example of the compound (1), each of $A^1$, $A^2$ and $A^3$ is

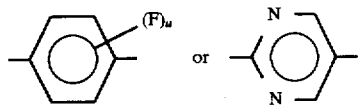

and desirably p is 1 and q is 0.

In another example of the compound (1), $R^1$ is an alkyl group or an alkenyl group, or $R^1$ is an alkoxyalkyl group, an alkenyloxyalkyl group, an alkoxyalkenyl group or an alkenyloxyalkenyl group.

In a further example of the compound (1), W is a hydrogen atom and X is —CH$_2$CH$_2$—.

In a yet another example of the compound (1), and one of $A^1$ and $A^2$ is

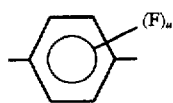

and the other of $A^1$ and $A^2$ is

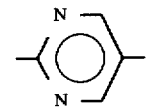

Specific examples of the compound of the formula (1) are

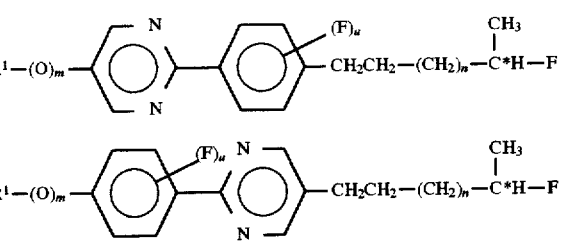

Specific examples of the compound of the formula (1) are as follows:
4''-Alkyl-4-(6-fluoro-1-heptynyl)-p-terphenyl,
4''-Alkyloxy-4-(6-fluoro-1-heptynyl)-p-terphenyl,
4'-Alkyl-4-(6-fluoro-1-heptynyl)-biphenyl,
4'-Alkyloxy-4-(6-fluoro-1-heptynyl)-biphenyl,
6-Alkyl-2-|4-(6-fluoro-1-heptynyl)-phenyl|naphthalene,
6-Alkyloxy-2-|4-(6-fluoro-1-heptynyl)-phenyl|naphthalene,
6-(4-Alkylphenyl)-2-(6-fluoro-1-heptynyl)naphthalene,
6-(4-Alkyloxyphenyl)-2-(6-fluoro-1-heptynyl)naphthalene,
2-Alkyl-6-(6-fluoro-1-heptynyl)naphthalene,
2-Alkyloxy-6-(6-fluoro-1-heptynyl)naphthalene,
5-Alkyl-|4-(6-fluoro-1-heptynyl)phenyl|pyridine,
5-Alkyloxy-|4-(6-fluoro-1-heptynyl)phenyl|pyridine,
2-(4-Alkylphenyl)-5-(6-fluoro-1-heptynyl)pyridine,
2-(4-Alkyloxyphenyl)-5-(6-fluoro-1-heptynyl)pyridine,
2-Alkyl-5-|4-(6-fluoro-1-heptynyl)phenyl|pyridine,
2-Alkyloxy-5-|4-(6-fluoro-1-heptynyl)phenyl|pyridine,
5-(4-Alkylphenyl)-2-(6-fluoro-1-heptynyl)pyridine,
5-(4-Alkyloxyphenyl)-2-(6-fluoro-1-heptynyl)pyridine,
5-Alkyl-2-|4'-(6-fluoro-1-heptynyl)-4-biphenylyl|pyridine,
5-Alkyloxy-2-|4'-(6-fluoro-1-heptynyl)-4-biphenylyl| pyridine,
2-(4'-Alkyl-4-biphenylyl)-5-(6-fluoro-1-heptynyl)pyridine,
2-(4'-Alkyloxy-4-biphenylyl)-5-(6-fluoro-1-heptynyl) pyridine,
5-(4-Alkylphenyl)-2-|4-(6-fluoro- 1-heptynyl)phenyl| pyridine,
5-(4-Alkyloxyphenyl)-2-|4-(6-fluoro-1-heptynyl)phenyl| pyridine,
2-(4-Alkylphenyl)-5-|4-(6-fluoro-1-heptynyl)phenyl| pyridine,
2-(4-Alkyloxyphenyl)-5-|4-(6-fluoro-1-heptynyl)phenyl| pyridine,
2-Alkyl-5-|6-(6-fluoro-1-heptynyl)naphthalen-2-yl| pyridine,
2-Alkyloxy-5-|6-(6-fluoro-1-heptynyl)naphthalen-2-yl| pyridine, 6-Alkyl-2-[6-(6-fluoro-1-heptynyl)naphthalen-2-yl]
pyridine.
6-Alkyloxy-2-[6-(6-fluoro-1-heptynyl)naphthalen-2-yl]
pyridine.
5-(6-Alkylnaphthalen-2-yl)-2-(6-fluoro-1-heptynyl)
pyridine.
5-(6-Alkyloxynaphthalen-2-yl)-2-(6-fluoro-1-heptynyl)
pyridine.
2-(6-Alkylnaphthalen-2-yl)-5-(6-fluoro-1-heptynyl)
pyridine.
2-(6-Alkyloxynaphthalen-2-yl)-5-(6-fluoro-1-heptynyl)
pyridine.
5-Alkyl-[4-(6-fluoro-1-heptynyl)phenyl]pyrimidine.
5-Alkyloxy-[4-(6-fluoro-1-heptynyl)-phenyl]pyrimidine.
2-(4-Alkylphenyl)-5-(6-fluoro-1-heptynyl)pyrimidine.
2-(4-Alkyloxyphenyl)-5-(6-fluoro-1-heptynyl)pyrimidine.
2-Alkyl-5-[4-(6-fluoro-1-heptynyl)phenyl]pyrimidine.
2-Alkyloxy-5-[4-(6-fluoro-1-heptynyl)phenyl]pyrimidine.
5-(4-Alkylphenyl)-2-(6-fluoro-1-heptynyl)pyrimidine.
5-(4-Alkyloxyphenyl)-2-(6-fluoro-1-heptynyl)pyrimidine.
5-Alkyl-2-[4'-(6-fluoro-1-heptynyl)-4-biphenylyl]
pyrimidine.
5-Alkyloxy-2-[4'-(6-fluoro-1-heptynyl)-4-biphenylyl]
pyrimidine.
2-(4'-Alkyl-4-biphenylyl)-5-(6-fluoro-1-heptynyl)
pyrimidine.
2-(4'-Alkyloxy-4-biphenylyl)-5-(6-fluoro-1-heptynyl)
pyrimidine.
5-(4-Alkylphenyl)-2-[4-(6-fluoro-1-heptynyl)phenyl]
pyrimidine.
5-(4-Alkyloxyphenyl)-2-[4-(6-fluoro-1-heptynyl)phenyl]
pyrimidine.
2-(4-Alkylphenyl)-5-[4-(6-fluoro-1-heptynyl)phenyl]
pyrimidine.
2-(4-Alkyloxyphenyl)-5-[4-(6-fluoro-1-heptynyl)phenyl]
pyrimidine.
5-Alkyl-[4-(6-fluoro-1-heptynyl)phenyl]-pyrazine.
5-Alkyloxy-[4-(6-fluoro-1-heptynyl)-phenyl]pyrazine.
2-(4-Alkylphenyl)-5-(6-fluoro-1-heptynyl)pyrazine.
2-(4-Alkyloxyphenyl)-5-(6-fluoro-1-heptynyl)phenyl]
pyrazine.
5-Alkyl-2-[4'-(6-fluoro-1-heptynyl)-4-biphenylyl]pyrazine.
5-Alkyloxy-2-[4'-(6-fluoro-1-heptynyl)-4-biphenylyl]
pyrazine.
2-(4'-Alkyl-4-biphenylyl)-5-(6-fluoro-1-heptynyl)pyrazine.
2-(4'-Alkyloxy-4-biphenylyl)-5-(6-fluoro-1-heptynyl)
pyrazine.
5-(4-Alkylphenyl)-2-[4-(6-fluoro-1-heptynyl)phenyl]
pyrazine.
5-(4-Alkyloxyphenyl)-2-[4-(6-fluoro-1-heptynyl)phenyl]
pyrazine.
3-(4-Alkylphenyl)-6-(6-fluoro-1-heptynyl)pyridazine.
3-(4-Alkyloxyphenyl)-6-(6-fluoro-1-heptynyl)pyridazine.
3-Alkyl-6-[4-(6-fluoro-1-heptynyl)]pyridazine. 3-Alkyloxy-
6-[4-(6-fluoro-1-heptynyl)]pyridazine.
6-(4-Alkylphenyl)-3-[4-(6-fluoro-1-heptynyl)phenyl]
pyridazine.
6-(4-Alkyloxyphenyl)-3-[4-(6-fluoro-1-heptynyl)phenyl]
pyridazine.
2-(6-Alkylnaphthalen-2-yl)-5-(6-fluoro-1-heptynyl)
pyrimidine.
2-(6-Alkyloxynaphthalen-2-yl)-5-(6-fluoro-1-heptynyl)
pyrimidine.
5-(6-Alkyl-naphthalen-2-yl)-2-(6-fluoro-1-heptynyl)
pyrimidine.
5-(6-Alkyloxy-naphthalen-2-yl)-2-(6-fluoro-1-heptynyl)
pyrimidine.

2-Alkyl-5-[6-(6-fluoro-1-heptynyl)naphthalen-2-yl]-
pyrimidine.
2-Alkyloxy-5-[6-(6-fluoro-1-heptynyl)naphthalen-2-yl]-
pyrimidine.
5-Alkyl-2-[6-(6-fluoro-1-heptynyl)naphthalen-1-yl]-
pyrimidine.
5-Alkyloxy-2-[6-(6-fluoro-1-heptynyl)naphthalen-1-yl]
pyrimidine.
7-Alkyl-3-[4-(6-fluoro-1-heptynyl)phenyl]-isoquinoline.
7-Alkyloxy-3-[4-(6-fluoro-1-heptynyl)phenyl]-
isoquinoline.
3-(4-Alkylphenyl)-7-(6-fluoro-1-heptynyl)isoquinoline.
3-(4-Alkyloxyphenyl)-7-(6-fluoro-1-heptynyl)-
isoquinoline.
6-Alkyl-2-[4-(6-fluoro-1-heptynyl)phenyl]quinoline.
6-Alkyloxy-2-[4-(6-fluoro-1-heptynyl)phenyl]quinoline.
2-(4-Alkylphenyl)-6-(6-fluoro-1-heptynyl)quinoline.
2-(4-Alkyloxyphenyl)-6-(6-fluoro-1-heptynyl)quinoline.
2-Alkyl-6-(6-fluoro-1-heptynyl)quinoxaline.
2-Alkyloxy-6-(6-fluoro-1-heptynyl)quinoxaline.
6-Alkyl-2-(6-fluoro-1-heptynyl)quinoxaline.
6-Alkyloxy-2-(6-fluoro-1-heptynyl)quinoxaline.
3-Alkyl-7-[4-(6-fluoro-1-heptynyl)phenyl]quinoxaline.
3-Alkyloxy-7-[4-(6-fluoro-1-heptynyl)phenyl]quinoxaline.
2-Alkyloxy-6-[4-(6-fluoro-1-heptynyl)phenyl]quinazoline.
4"-Alkyl-4-(6-fluoro-1-heptyl)-p-terphenyl.
4"-Alkyloxy-4-(6-fluoro-1-heptyl)-p-terphenyl.
4'-Alkyl-4-(6-fluoro-1-heptyl)biphenyl.
4'-Alkyloxy-4-(6-fluoro-1-heptyl)biphenyl.
6-Alkyl-2-[4-(6-fluoro-1-heptyl)phenyl]naphthalene.
6-Alkyloxy-2-[4-(6-fluoro-1-heptyl)phenyl]naphthalene.
6-(4-Alkylphenyl)-2-(6-fluoro-1-heptyl)naphthalene.
6-(4-Alkyloxyphenyl)-2-(6-fluoro-1-heptyl)naphthalene.
2-Alkyl-6-(6-fluoro-1-heptyl)naphthalene.
2-Alkyloxy-6-(6-fluoro-1-heptyl)naphthalene.
5-Alkyl-[4-(6-fluoro-1-heptyl)phenyl]pyridine.
5-Alkyloxy-[4-(6-fluoro-1-heptyl)phenyl]pyridine.
2-(4-Alkylphenyl)-5-(6-fluoro-1-heptyl)pyridine.
2-(4-Alkyloxyphenyl)-5-(6-fluoro-1-heptyl)pyridine.
2-Alkyl-5-[4-(6-fluoro-1-heptyl)phenyl]pyridine.
2-Alkyloxy-5-[4-(6-fluoro-1-heptyl)phenyl]pyridine.
5-(4-Alkylphenyl)-2-(6-fluoro-1-heptyl)pyridine.
5-(4-Alkyloxyphenyl)-2-(6-fluoro-1-heptyl)pyridine.
5-Alkyl-2-[4'-(6-fluoro-1-heptyl)-4-biphenylyl]pyridine.
5-Alkyloxy-2-[4'-(6-fluoro-1-heptyl)-4-biphenylyl]
pyridine.
2-(4'-Alkyl-4-biphenylyl)-5-(6-fluoro-1-heptyl)pyridine.
2-(4'-Alkyloxy-4-biphenylyl)-5-(6-fluoro-1-heptyl)
pyridine.
5-(4-Alkylphenyl)-2-[4-(6-fluoro-1-heptyl)phenyl]pyridine.
5-(4-Alkyloxyphenyl)-2-[4-(6-fluoro-1-heptyl)phenyl]
pyridine.
2-(4-Alkylphenyl)-5-[4-(6-fluoro-1-heptyl)phenyl]pyridine.
2-(4-Alkyloxyphenyl)-5-[4-(6-fluoro-1-heptyl)phenyl]
pyridine.
2-Alkyl-5-[6-(6-fluoro-1-heptyl)naphthalen-2-yl]pyridine.
2-Alkyloxy-5-[6-(6-fluoro-1-heptyl)naphthalen-2-yl]
pyridine.
6-Alkyl-2-[6-(6-fluoro-1-heptyl)naphthalen-2-yl]pyridine.
6-Alkyloxy-2-[6-(6-fluoro-1-heptyl)naphthalen-2-yl]
pyridine.
5-(6-Alkylnaphthalen-2-yl)-2-(6-fluoro-1-heptyl)pyridine.
5-(6-Alkyloxynaphthalen-2-yl)-2-(6-fluoro-1-heptyl)
pyridine.
2-(6-Alkyl-naphthalen-2-yl)-5-(6-fluoro-1-heptyl)pyridine.
2-(6-Alkyloxy-naphthalen-2-yl)-5-(6-fluoro-1-heptyl)
pyridine.

5-Alkyl-[4-(6-fluoro-1-heptyl)phenyl]pyrimidine.
5-Alkyloxy-[4-(6-fluoro-1-heptyl)phenyl]pyrimidine.
2-(4-Alkylphenyl)-5-(6-fluoro-1-heptyl)pyrimidine.
2-(4-Alkyloxyphenyl)-5-(6-fluoro-1-heptyl)pyrimidine.
2-Alkyl-5-[4-(6-fluoro-1-heptyl)phenyl]pyrimidine.
2-Alkyloxy-5-[4-(6-fluoro-1-heptyl)phenyl]pyrimidine.
5-(4-Alkylphenyl)-2-(6-fluoro-1-heptyl)pyrimidine.
5-(4-Alkyloxyphenyl)-2-(6-fluoro-1-heptyl)pyrimidine.
5-Alkyl-2-[4'-(6-fluoro-1-heptyl)-4-biphenylyl]pyrimidine.
5-Alkyloxy-2-[4'-(6-fluoro-1-heptyl)-4-biphenylyl]pyrimidine.
2-(4'-Alkyl-4-biphenylyl)-5-(6-fluoro-1-heptyl)pyrimidine.
2-(4'-Alkyloxy-4-biphenylyl)-5-(6-fluoro-1-heptyl)pyrimidine.
5-(4-Alkylphenyl)-2-[4-(6-fluoro-1-heptyl)phenyl]pyrimidine.
5-(4-Alkyloxyphenyl)-2-[4-(6-fluoro-1-heptyl)phenyl]pyrimidine.
2-(4-Alkylphenyl)-5-[4-(6-fluoro-1-heptyl)phenyl]pyrimidine.
2-(4-Alkyloxyphenyl)-5-[4-(6-fluoro-1-heptyl)phenyl]pyrimidine.
5-Alkyl-[4-(6-fluoro-1-heptyl)phenyl]pyrazine.
5-Alkyloxy-[4-(6-fluoro-1-heptyl)phenyl]pyrazine.
2-(4-Alkylphenyl)-5-(6-fluoro-1-heptyl)pyrazine.
2-(4-Alkyloxyphenyl)-5-(6-fluoro-1-heptyl)pyrazine.
5-Alkyl-2-[4'-(6-fluoro-1-heptyl)-4-biphenylyl]pyrazine.
5-Alkyloxy-2-[4'-(6-fluoro-1-heptyl)-4-biphenylyl]pyrazine.
2-(4'-Alkyl-4-biphenylyl)-5-(6-fluoro-1-heptyl)pyrazine.
2-(4'-Alkyloxy-4-biphenylyl)-5-(6-fluoro-1-heptyl)pyrazine.
5-(4-Alkylphenyl)-2-[4-(6-fluoro-1-heptyl)phenyl]pyrazine.
5-(4-Alkyloxyphenyl)-2-[4-(6-fluoro-1-heptyl)phenyl]pyrazine.
3-(4-Alkylphenyl)-6-(6-fluoro-1-heptyl)pyridazine.
3-(4-Alkyloxyphenyl)-6-(6-fluoro-1-heptyl)pyridazine.
3-Alkyl-6-[4-(6-fluoro-1-heptyl)]pyridazine.
3-Alkyloxy-6-[4-(6-fluoro-1-heptyl)]pyridazine.
6-(4-Alkylphenyl)-3-[4-(6-fluoro-1-heptyl)phenyl]pyridazine.
6-(4-Alkyloxyphenyl)-3-[4-(6-fluoro-1-heptyl)phenyl]pyridazine.
2-(6-Alkylnaphthalen-2-yl)-5-(6-fluoro-1-heptyl)pyrimidine.
2-(6-Alkyloxynaphthalen-2-yl)-5-(6-fluoro-1-heptyl)pyrimidine.
5-(6-Alkylnaphthalen-2-yl)-2-(6-fluoro-1-heptyl)pyrimidine.
5-(6-Alkyloxynaphthalen-2-yl)-2-(6-fluoro-1-heptyl)pyrimidine.
2-Alkyl-5-[6-(6-fluoro-1-heptyl)naphthalene-2-yl]pyrimidine.
2-Alkyloxy-5-[6-(6-fluoro-1-heptyl)naphthalene-2-yl]pyrimidine.
5-Alkyl-2-[6-(6-fluoro-1-heptyl)naphthalene-2-yl]pyrimidine.
5-Alkyloxy-2-[6-(6-fluoro-1-heptyl)naphthalene-2-yl]pyrimidine.
7-Alkyl-3-[4-(6-fluoro-1-heptyl)phenyl]isoquinoline.
7-Alkyloxy-3-[4-(6-fluoro-1-heptyl)phenyl]isoquinoline.
3-(4-Alkylphenyl)-7-(6-fluoro-1-heptyl)isoquinoline.
3-(4-Alkyloxyphenyl)-7-(6-fluoro-1-heptyl)isoquinoline.
6-Alkyl-2-[4-(6-fluoro-1-heptyl)phenyl]quinoline.
6-Alkyloxy-2-[4-(6-fluoro-1-heptyl)phenyl]quinoline.
2-(4-Alkylphenyl)-6-(6-fluoro-1-heptyl)quinoline.
2-(4-Alkyloxyphenyl)-6-(6-fluoro-1-heptyl)quinoline.

2-Alkyl-6-(6-fluoro-1-heptyl)quinoxaline.
2-Alkyloxy-6-(6-fluoro-1-heptyl)quinoxaline.
6-Alkyl-2-(6-fluoro-1-heptyl)quinoxaline.
6-Alkyloxy-2-(6-fluoro-1-heptyl)quinoxaline.
3-Alkyl-7-[4-(6-fluoro-1-heptyl)phenyl]quinoxaline.
3-Alkyloxy-7-[4-(6-fluoro-1-heptyl)phenyl]quinoxaline.
2-Alkyloxy-6-[4-(6-fluoro-1-heptyl)phenyl]quinazoline.
4"-Alkyl-4-(6-fluoro-1-heptenyl)-p-terphenyl.
4"-Alkyloxy-4-(6-fluoro-1-heptenyl)-p-terphenyl.
4'-Alkyl-4-(6-fluoro-1-heptenyl)biphenyl.
4'-Alkyloxy-4-(6-fluoro-1-heptenyl)biphenyl.
6-Alkyl-2-[4-(6-fluoro-1-heptenyl)phenyl]naphthalene.
6-Alkyloxy-2-[4-(6-fluoro-1-heptenyl)phenyl]naphthalene.
6-(4-Alkylphenyl)-2-(6-fluoro-1-heptenyl)naphthalene.
6-(4-Alkyloxyphenyl)-2-(6-fluoro-1-heptenyl)naphthalene.
2-Alkyl-6-(6-fluoro-1-heptenyl)naphthalene.
2-Alkyloxy-6-(6-fluoro-1-heptenyl)naphthalene.
5-Alkyl-[4-(6-fluoro-1-heptenyl)phenyl]pyridine.
5-Alkyloxy-[4-(6-fluoro-1-heptenyl)phenyl]pyridine.
2-(4-Alkylphenyl)-5-(6-fluoro-1-heptenyl)pyridine.
2-(4-Alkyloxyphenyl)-5-(6-fluoro-1-heptenyl)pyridine.
2-Alkyl-5-[4-(6-fluoro-1-heptenyl)phenyl]pyridine.
2-Alkyloxy-5-[4-(6-fluoro-1-heptenyl)phenyl]pyridine.
5-(4-Alkylphenyl)-2-(6-fluoro-1-heptenyl)pyridine.
5-(4-Alkyloxyphenyl)-2-(6-fluoro-1-heptenyl)pyridine.
5-Alkyl-2-[4'-(6-fluoro-1-heptenyl)-4-biphenylyl]pyridine.
5-Alkyloxy-2-[4'-(6-fluoro-1-heptenyl)-4-biphenylyl]pyridine.
2-(4'-Alkyl-4-biphenylyl)-5-(6-fluoro-1-heptenyl)pyridine.
2-(4'-Alkyloxy-4-biphenylyl)-5-(6-fluoro-1-heptenyl)pyridine.
5-(4-Alkylphenyl)-2-[4-(6-fluoro-1-heptenyl)phenyl]pyridine.
5-(4-Alkyloxyphenyl)-2-[4-(6-fluoro-1-heptenyl)phenyl]pyridine.
2-(4-Alkylphenyl)-5-[4-(6-fluoro-1-heptenyl)phenyl]pyridine.
2-(4-Alkyloxyphenyl)-5-[4-(6-fluoro-1-heptenyl)phenyl]pyridine.
2-Alkyl-5-[6-(6-fluoro-1-heptenyl)naphthalen-2-yl]pyridine.
2-Alkyloxy-5-[6-(6-fluoro-1-heptenyl)naphthalen-2-yl]pyridine.
6-Alkyl-2-[6-(6-fluoro-1-heptenyl)naphthalen-2-yl]pyridine.
6-Alkyloxy-2-[6-(6-fluoro-1-heptenyl)naphthalen-2-yl]pyridine.
5-(6-Alkylnaphthalen-2-yl)-2-(6-fluoro-1-heptenyl)pyridine.
5-(6-Alkyloxynaphthalen-2-yl)-2-(6-fluoro-1-heptenyl)pyridine.
2-(6-Alkylnaphthalen-2-yl)-5-(6-fluoro-1-heptenyl)pyridine.
2-(6-Alkyloxynaphthalen-2-yl)-5-(6-fluoro-1-heptenyl)pyridine.
5-Alkyl-[4-(6-fluoro-1-heptenyl)phenyl]pyrimidine.
5-Alkyloxy-[4-(6-fluoro-1-heptenyl)phenyl]pyrimidine.
2-(4-Alkylphenyl)-5-(6-fluoro-1-heptenyl)pyrimidine.
2-(4-Alkyloxyphenyl)-5-(6-fluoro-1-heptenyl)pyrimidine.
2-Alkyl-5-[4-(6-fluoro-1-heptenyl)phenyl]pyrimidine.
2-Alkyloxy-5-[4-(6-fluoro-1-heptenyl)phenyl]pyrimidine.
5-(4-Alkylphenyl)-2-(6-fluoro-1-heptenyl)pyrimidine.
5-(4-Alkyloxyphenyl)-2-(6-fluoro-1-heptenyl)pyrimidine.
5-Alkyl-2-[4'-(6-fluoro-1-heptenyl)-4-biphenylyl]pyrimidine.
5-Alkyloxy-2-[4'-(6-fluoro-1-heptenyl)-4-biphenylyl]pyrimidine.

2-(4'-Alkyl-4-biphenylyl)-5-(6-fluoro-1-heptenyl)pyrimidine,
2-(4'-Alkyloxy-4-biphenylyl)-5-(6-fluoro-1-heptenyl)pyrimidine,
5-(4-Alkylphenyl)-2-[4-(6-fluoro-1-heptenyl)phenyl]pyrimidine,
5-(4-Alkyloxyphenyl)-2-[4-(6-fluoro-1-heptenyl)phenyl]pyrimidine
2-(4-Alkylphenyl)-5-[4-(6-fluoro-1-heptenyl)phenyl]pyrimidine
2-(4-Alkyloxyphenyl)-5-[4-(6-fluoro-1-heptenyl)phenyl]pyrimidine,
5-Alkyl-[4-(6-fluoro-1-heptenyl)phenyl]pyrazine,
5-Alkyloxy-[4-(6-fluoro-1-heptenyl)phenyl]pyrazine,
2-(4-Alkylphenyl)-5-(6-fluoro-1-heptenyl)pyrazine,
2-(4-Alkyloxyphenyl)-5-(6-fluoro-1-heptenyl)pyrazine,
5-Alkyl-2-[4'-(6-fluoro-1-heptenyl)-4-biphenylyl]pyrazine,
5-Alkyloxy-2-[4'-(6-fluoro-1-heptenyl)-4-biphenylyl]pyrazine,
2-(4'-Alkyl-4-biphenylyl)-5-(6-fluoro-1-heptenyl)pyrazine,
2-(4'-Alkyloxy-4-biphenylyl)-5-(6-fluoro-1-heptenyl)pyrazine,
5-(4-Alkylphenyl)-2-[4-(6-fluoro-1-heptenyl)phenyl]pyrazine,
5-(4-Alkyloxyphenyl)-2-[4-(6-fluoro-1-heptenyl)phenyl]pyrazine,
3-(4-Alkylphenyl)-6-(6-fluoro-1-heptenyl)pyridazine,
3-(4-Alkyloxyphenyl)-6-(6-fluoro-1-heptenyl)pyridazine,
3-Alkyl-6-[4-(6-fluoro-1-heptenyl)]pyridazine,
3-Alkyloxy-6-[4-(6-fluoro-1-heptenyl)]pyridazine,
6-(4-Alkylphenyl)-3-[4-(6-fluoro-1-heptenyl)phenyl]pyridazine,
6-(4-Alkyloxyphenyl)-3-[4-(6-fluoro-1-heptenyl)phenyl]pyridazine,
2-(6-Alkylnaphthalen-2-yl)-5-(6-fluoro-1-heptenyl)pyrimidine,
2-(6-Alkyloxynaphthalen-2-yl)-5-(6-fluoro-1-heptenyl)pyrimidine,
5-(6-Alkylnaphthalen-2-yl)-2-(6-fluoro-1-heptenyl)pyrimidine,
5-(6-Alkyloxynaphthalen-2-yl)-2-(6-fluoro-1-heptenyl)pyrimidine,
2-Alkyl-5-[6-(6-fluoro-1-heptenyl)naphthalen-2-yl]pyrimidine,
2-Alkyloxy-5-[6-(6-fluoro-1-heptenyl)naphthalen-2-yl]pyrimidine,
5-Alkyl-2-[6-(6-fluoro-1-heptenyl)naphthalen-2-yl]pyrimidine,
5-Alkyloxy-2-[6-(6-fluoro-1-heptenyl)naphthalen-2-yl]pyrimidine,
7-Alkyl-3-[4-(6-fluoro-1-heptenyl)phenyl]isoquinoline,
7-Alkyloxy-3-[4-(6-fluoro-1-heptenyl)phenyl]isoquinoline,
3-(4-Alkylphenyl)-7-(6-fluoro-1-heptenyl)isoquinoline,
3-(4-Alkyloxyphenyl)-7-(6-fluoro-1-heptenyl)isoquinoline,
6-Alkyl-2-[4-(6-fluoro-1-heptenyl)phenyl]quinoline,
6-Alkyloxy-2-[4-(6-fluoro-1-heptenyl)phenyl]quinoline,
2-(4-Alkylphenyl)-6-(6-fluoro-1-heptenyl)quinoline,
2-(4-Alkyloxyphenyl)-6-(6-fluoro-1-heptenyl)quinoline,
2-Alkyl-6-(6-fluoro-1-heptenyl)quinoxaline,
2-Alkyloxy-6-(6-fluoro-1-heptenyl)quinoxaline,
6-Alkyl-2-(6-fluoro-1-heptenyl)quinoxaline,
6-Alkyloxy-2-(6-fluoro-1-heptenyl)quinoxaline,
3-Alkyl-7-[4-(6-fluoro-1-heptenyl)phenyl]quinoxaline,
3-Alkyloxy-7-[4-(6-fluoro-1-heptenyl)phenyl]quinoxaline,
2-Alkyloxy-6-[4-(6-fluoro-1-heptenyl)phenyl]quinazoline,
the above compounds in which each of the 6-fluoro-1-heptynyl group, the 6-fluoro-1-heptyl group or the 6-fluoro-heptenyl group is respectively replaced by a 4-fluoro-1-pentynyl, 5-fluoro-1-hexynyl, 7-fluoro-1-octynyl, 8-fluoro-1-nonynyl, 9-fluoro-1-decynyl, 10-fluoro-1-undecynyl, 11-fluoro-1-dodecynyl, 12-fluoro-1-tridecynyl or 13-fluoro-1-tetradecynyl group; a 4-fluoro-1-pentyl, 5-fluoro-1-hexyl, 7-fluoro-1-octyl, 8-fluoro-1-nonyl, 9-fluoro-1-decyl, 10-fluoro-1-undecyl, 11-fluoro-1-dodecyl, 12-fluoro-1-tridecyl or 13-fluoro-1-tetradecyl group; or a 4-fluoro-1-pentenyl, 5-fluoro-1-hexenyl, 7-fluoro-1-octenyl, 8-fluoro-1-nonenyl, 9-fluoro-1-decenyl, 10-fluoro-1-undecenyl, 11-fluoro-1-dodecenyl, 12-fluoro-1-tridecenyl or 13-fluoro-1-tetradecenyl, the above compounds in which hydrogen atoms of a terminal methyl group are replaced by fluorine atoms, the above compounds in which one, two or three hydrogens of a benzene ring are replaced by one, two or three fluorine atoms, the above compounds in which an alkyl group or an alkyloxy group is respectively replaced by an alkenyl group or an alkenyloxy group, and the above compounds in which an alkyl group or an alkyloxy group is replaced by an alkoxyalkyl, alkenyloxyalkyl, alkoxyalkenyl, alkenyloxyalkenyl, alkoxyalkoxy, alkenyloxyalkoxy, alkoxyalkenyloxy or alkenyloxyalkenyloxy group.

Herein, the alkyl, alkyloxy, alkenyl, alkenyloxy, alkoxyalkyl, alkenyloxyalkyl, alkoxyalkenyl, alkenyloxyalkenyl, alkoxyalkoxy, alkenyloxyalkoxy, alkoxyalkenyloxy or alkenyloxyalkenyloxy group has 3 to 20 carbon atoms.

While the fluorine-containing optically active compound (1) of the present invention as such has good properties as the liquid crystal, it can be mixed with at least one compound having a Sc phase to provide, in particular, a ferroelectric liquid crystal mixture having good properties.

The compound having the Sc phase to be used in combination with the fluorine-containing optically active compound of the present invention is not limited. Examples of the compound having the Sc phase are azomethine compounds, Schiff's base compounds, azo or azoxy type compounds, biphenyl type compounds, aromatic ester type compounds, phenylpyrimidine type compounds, and the like.

In the liquid crystal mixture of the present invention, an amount of the fluorine-containing optically active compound (1) of the present invention is from 1 to 95% by mol, preferably from 2 to 50% by mol based on one mol of the liquid crystal mixture.

In addition to the use as a component of a low viscosity liquid crystal material or as a chiral dopant, the fluorine-containing optically active compound (1) of the present invention can be used in the field of agrochemicals and pharmaceuticals, for example, as an intermediate.

PREFERRED EMBODIMENTS OF THE INVENTION

The present invention will be illustrated by the following Examples, which do not limit the scope of the present invention in any way.

In the following phase sequences, K represents a crystal, Sc* represents a chiral smectic C phase, $S_A$ represents a smectic A phase, I represents an isotropic phase, and Ch represents Cholesteric phase.

EXAMPLE 1

In a reactor equipped with a stirrer and a thermometer, (−)-5-decyloxy-2-[4-(6-hydroxyheptyl)phenyl]pyrimidine (1.0 g) and dichloromethane (40 ml) are charged. To the mixture. diethylaminosulfur trifluoride (0.5 g) is added at −50° C.. followed by stirring for 30 minutes.

The reaction mixture is poured in water and extracted with toluene (100 ml). The organic layer is washed with water and evaporated under reduced pressure. A resulting residue is purified by silica gel column chromatography (eluent: toluene-hexene) to obtain 5-decyloxy-2-|4-(6-fluoroheptyl)phenyl|pyrimidine (0.7 g). Phase sequences:

K-34° C.-Sc*-74° C.-I

EXAMPLE 2

In a reactor equipped with a stirrer and a thermometer. (−)-5-decyloxy-2-|4-(4-hydroxypentyl)phenyl|pyrimidine (0.5 g) and dichloromethane (20 ml) are charged. To the mixture. diethylaminosulfur trifluoride (0.2 g) is added at −50° C.. followed by stirring for 1 hour.

The reaction mixture is poured in water and extracted with toluene (50 ml). The organic layer is washed with water and evaporated under reduced pressure. A resulting residue is purified by silica gel column chromatography (eluent: hexane-ethyl acetate) to obtain 5-decyloxy-2-|4-(4-fluoropentyl)phenyl|pyrimidine (0.3 g). Phase sequences:

K-43° C.-Sc*-61° C.-S$_A$-70° C.-I

EXAMPLE 3

In a reactor equipped with a stirrer and a thermometer. (−)-2-decyloxy-5-(6-hydroxyheptyl)pyrimidine (1.0 g) and dichloromethane (40 ml) are charged. To the mixture. diethylaminosulfur trifluoride (0.5 g) is added at −50° C.. followed by stirring for 30 minutes.

The reaction mixture is poured in water and extracted with toluene (100 ml). The organic layer is washed with water and evaporated under reduced pressure. A resulting residue is purified by silica gel column chromatography (eluent: toluene-hexane) to obtain 2-decyloxyphenyl-5-(6-fluoroheptyl)pyrimidine (0.7 g). Clearing point: 62° C.

```
K――――47° C.―S_A-61° C.-Ch-62° C.-I
|                                  |
21° C.-Sc*-30° C.
```

EXAMPLE 4

In a reactor equipped with a stirrer and a thermometer. (−)-5-decyloxy-2-|4-(6-hydroxyheptyl)-2.3-difluorophenyl] pyrimidine (1.0 g) and dichloromethane (40 ml) are charged. To the mixture. diethylaminosulfur trifluoride (0.5 g) is added at −50° C.. followed by stirring for 30 minutes.

The reaction mixture is poured in water and extracted with toluene (100 ml). The organic layer is washed with water and evaporated under reduced pressure. A resulting residue is purified by silica gel column chromatography (eluent: toluene-hexane) to obtain 5-decyloxy-2-|4-(6-fluoroheptyl)-2.3-difluorophenyl|pyrimidine.

EXAMPLE 5

In a reactor equipped with a stirrer and a thermometer. (−)-2-(4-decyloxy-2.3-difluoro)phenyl-5-(6-hydroxyheptyl) pyrimidine (1.0 g) and dichloromethane (40 ml) are charged. To the mixture. diethylaminosulfur trifluoride (0.5 g) is added at −50° C.. followed by stirring for 30 minutes.

The reaction mixture is poured in water and extracted with toluene (100 ml). The organic layer is washed with water and evaporated under reduced pressure. A resulting residue is purified by silica gel column chromatography (eluent: toluene-hexane) to obtain 2-(4-decyloxy-2.3-difluoro)phenyl-5-(6-fluoroheptyl)pyrimidine (0.75 g).

```
K――――52° C.――――|
|              |
20° C.-S_A-34° C.-Ch-38° C.
```

EXAMPLE 6

In a reactor equipped with a stirrer and a thermometer. (−)-5-decyloxy-2-|4-(7-hydroxyoctyl)-2-fluorophenyl| pyrimidine (1.0 g) and dichloromethane (40 ml) are charged. To the mixture. diethylaminosulfur trifluoride (0.5 g) is added at −40° C.. followed by stirring for 30 minutes.

The reaction mixture is poured in water and extracted with toluene (100 ml). The organic layer is washed with water and evaporated under reduced pressure. A resulting residue is purified by silica gel column chromatography (eluent: toluene-hexane) to obtain 5-decyloxy-2-|4-(7-fluorooctyl)-2-fluorophenyl|pyrimidine.

EXAMPLE 7

In a reactor equipped with a stirrer and a thermometer. (−)-5-decyloxy-2-|4-(6-hydroxyheptyl)-2-fluorophenyl| pyrimidine (0.1 g) and dichloromethane (10 ml) are charged. To the mixture. diethylaminosulfur trifluoride (0.1 g) is added at −50° C.. followed by stirring for 1 hour.

The reaction mixture is poured in water and extracted with toluene (50 ml). The organic layer is washed with water and evaporated under reduced pressure. A resulting residue is purified by silica gel column chromatography (eluent: hexane-ethyl acetate) to obtain 5-decyloxy-2-|4-(6-fluoroheptyl)phenyl|pyrimidine (0.09 g). Phase sequences:

K-25° C.-Sc*-28° C.-S$_A$-42° C.-I

EXAMPLE 8

In a reactor equipped with a stirrer and a thermometer. (−)-2-(4-decyloxy-2-fluoro)phenyl-5-(5-hydroxyhexyl) pyrimidine (1.0 g) and dichloromethane (40 ml) are charged. To the mixture. diethylaminosulfur trifluoride (0.5 g) is added at −50° C.. followed by stirring for 30 minutes.

The reaction mixture is poured in water and extracted with toluene (100 ml). The organic layer is washed with water and evaporated under reduced pressure. A resulting residue is purified by silica gel column chromatography (eluent: toluene-hexane) to obtain 2-(4-decyloxy-2-fluoro) phenyl-5-(6-fluoroheptyl)pyrimidine.

EXAMPLE 9

In a reactor equipped with a stirrer and a thermometer. (−)-5-(1-nonenyl)-2-|4-(6-hydroxyheptyl)phenyl| pyrimidine (1.0 g) and dichloromethane (40 ml) are charged. To the mixture. diethylaminosulfur trifluoride (0.5 g) is added at −70° C.. followed by stirring for 60 minutes.

The reaction mixture is poured in water and extracted with toluene (100 ml). The organic layer is washed with water and evaporated under reduced pressure. A resulting residue is purified by silica gel column chromatography (eluent: toluene-hexane) to obtain 5-(1-nonenyl)-2-|4-(6-fluoroheptyl)phenyl|pyrimidine.

EXAMPLE 10

In a reactor equipped with a stirrer and a thermometer. (−)-2-|4-(1-nonenyl)phenyl-5-(6-hydroxyheptyl)pyrimidine (1.0 g) and dichloromethane (40 ml) are charged. To the mixture, diethylaminosulfur trifluoride (0.5 g) is added at −70° C., followed by stirring for 60 minutes.

The reaction mixture is poured in water and extracted with toluene (100 ml). The organic layer is washed with water and evaporated under reduced pressure. A resulting residue is purified by silica gel column chromatography (eluent: toluene-hexane) to obtain 2-[4-(1-nonenyl)phenyl-5-(6-fluoroheptyl)pyrimidine.

EXAMPLE 11

In a reactor equipped with a stirrer and a thermometer, (−)-5-(1-nonenyl)-2-[4-(6-hydroxyheptyl)-2,3-difluorophenyl]pyrimidine (1.0 g) and dichloromethane (40 ml) are charged. To the mixture, diethylaminosulfur trifluoride (0.5 g) is added at −70° C., followed by stirring for 30 minutes.

The reaction mixture is poured in water and extracted with toluene (100 ml). The organic layer is washed with water and evaporated under reduced pressure. A resulting residue is purified by silica gel column chromatography (eluent: toluene-hexane) to obtain 5-(1-nonenyl)-2-[4-(6-fluoroheptyl)-2,3-difluorophenyl]pyrimidine.

EXAMPLE 12

In a reactor equipped with a stirrer and a thermometer, (−)-2-[4-(1-nonenyl)-2,3-difluorophenyl]-5-(6-hydroxyheptyl)pyrimidine (1.0 g) and dichloromethane (40 ml) are charged. To the mixture, diethlaminosulfur trifluoride (0.5 g) is added at −50° C., followed by stirring for 60 minutes.

The reaction mixture is poured in water and extracted with toluene (100 ml). The organic layer is washed with water and evaporated under reduced pressure. A resulting residue is purified by silica gel column chromatography (eluent: toluene-hexane) to obtain 2-[4-(1-nonenyl)-2,3-difluorophenyl]-5-(6-fluoroheptyl)pyrimidine.

EXAMPLES 13–80

In the same manner as in Example 1 except that a raw material alcohol derivative and a fluorinating agent shown in Tables 1–12 are used and a reaction condition indicated in Tables 1–12 is employed, the reaction and post-treatment are carried out to obtain a desired compound.

Measurement of liquid crystal property

The compound prepared in Example 1 is inserted between a pair of glass plates inner surfaces of which are coated with a transparent electrode and a polyimide orientation film, with placing a spacer between the glass plates to form a gap of 2 μm.

On outer sides of the glass plates, respective polarization plates were provided with their polarization planes being twisted at an angle of 90°, to set up a liquid crystal element.

A polarization axis on a light-incident side is set to coincide with a rubbing direction of the polyamide orientation film.

To this liquid crystal element, a rectangular wave of ±20 V is applied and an optical response is detected to measure a response time. The response time is defined as a width of half maximum of polarization current peak.

The response time is 10 μsec. at 40° C. and 8 μsec. at 60° C.

TABLE 1

| Example No. | Alcohol derivative (2) | | | X | n | W | Fluorinating agent & Reaction condition |
|---|---|---|---|---|---|---|---|
| | $R^1-(O)_m-$ | $-A^1-(A^2)_p-(A^3)_q-$ | | | | | |
| 13 | $C_{10}H_{21}O-$ | 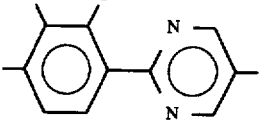 | |  E | 3 | H | Dichloromethane DAST |
| 14 | $C_{10}H_{21}O-$ | 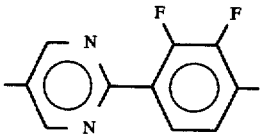 | | $-\equiv-$ | 3 | H | Dichloromethane DAST |
| 15 | $C_8H_{17}O-$ | 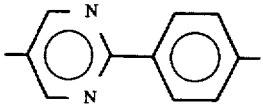 | | $-CH_2CH_2-$ | 5 | H | Dichloromethane Morph-DAST |
| 16 | $C_{11}H_{23}O-$ | 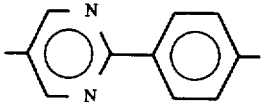 | |  E | 3 | H | Dichloromethane DAST |

TABLE 1-continued

| Example No. | Alcohol derivative (2) | | X | n | W | Fluorinating agent & Reaction condition |
|---|---|---|---|---|---|---|
| | $R^1-(O)_m-$ | $-A^1-(A^2)_p-(A^3)_q-$ | | | | |
| 17 | $C_{10}H_{21}-$ | 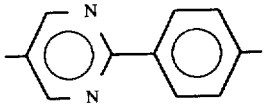 |  E | 3 | H | Dichloromethane DAST |
| 18 | $C_9H_{19}O-$ | 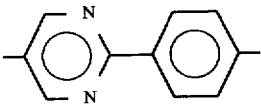 | $-CH_2CH_2-$ | 5 | H | Dichloroethane Morph-DAST |

TABLE 2

| Example No. | Alcohol derivative (2) | | X | n | W | Fluorinating agent & Reaction condition |
|---|---|---|---|---|---|---|
| | $R^1-(O)_m-$ | $-A^1-(A^2)_p-(A^3)_q-$ | | | | |
| 19 | $C_8H_{17}-$ | 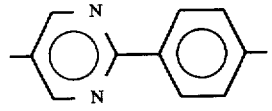 | $-CH_2CH_2-$ | 3 | H | Dichloroethane Morph-DAST |
| 20 | $C_7H_{15}O-$ | 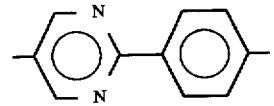 | $-CH_2CH_2-$ | 3 | H | Dichloroethane Morph-DAST |
| 21 | $C_6H_{13}O-$ | 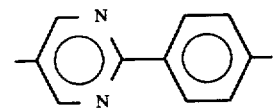 | $-CH_2CH_2-$ | 3 | H | Dichloroethane Morph-DAST |
| 22 | $C_4H_9O-$ | 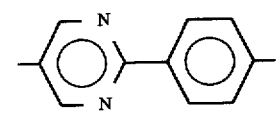 | $-CH_2CH_2-$ | 3 | F | Dichloroethane Morph-DAST |
| 23 | $C_{12}H_{25}-$ | 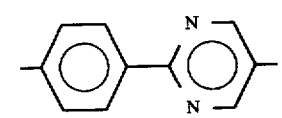 | $-CH_2CH_2-$ | 3 | H | Dichloroethane Morph-DAST |
| 24 | $C_9H_{19}O-$ | 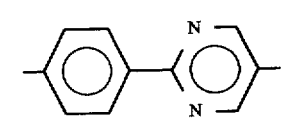 |  E | 3 | H | Dichloromethane DAST |

TABLE 3

| Example No. | Alcohol derivative (2) R¹—(O)ₘ— | —A¹—(A²)ₚ—(A³)q— | X | n | W | Fluorinating agent & Reaction condition |
|---|---|---|---|---|---|---|
| 25 | $C_8H_{17}O-$ | 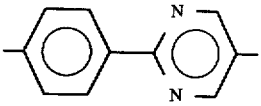 | —≡— | 3 | H | Dichloromethane DAST |
| 26 | $C_7H_{15}O-$ | 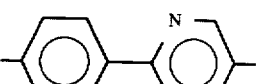 | $-CH_2CH_2-$ | 3 | H | Dochloromethane DAST |
| 27 | $C_{11}H_{23}O-$ | 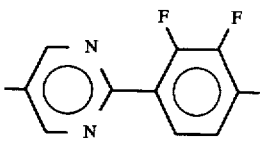 |  E | 3 | H | Dichloromethane DAST |
| 28 | $C_{12}H_{25}O-$ | 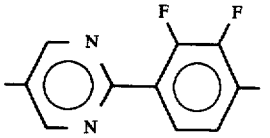 | $-CH_2CH_2-$ | 3 | F | Dichloromethane DAST |
| 29 | $C_{12}H_{25}O-$ | 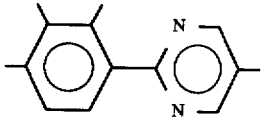 | $-CH_2CH_2-$ | 3 | H | Dichloromethane DAST |
| 30 | $C_9H_{19}O-$ | 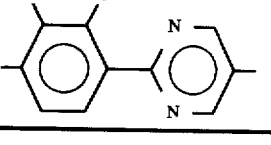 | $-CH_2CH_2-$ | 5 | H | Dichloromethane DAST |

TABLE 4

| Example No. | Alcohol derivative (2) R¹—(O)ₘ— | —A¹—(A²)ₚ—(A³)q— | X | n | W | Fluorinating agent & Reaction condition |
|---|---|---|---|---|---|---|
| 31 | $C_8H_{17}O-$ | 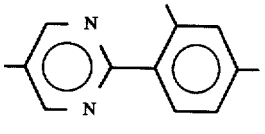 | $-CH_2CH_2-$ | 3 | H | Same as in Example 1 |
| 32 | $C_9H_{19}O-$ | 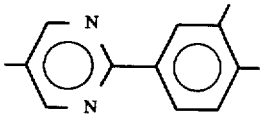 | $-CH_2CH_2-$ | 3 | H | Same as in Example 1 |

TABLE 4-continued

| Example No. | Alcohol derivative (2) $R^1-(O)_m-$ | $-A^1-(A^2)_p-(A^3)_q-$ | X | n | W | Fluorinating agent & Reaction condition |
|---|---|---|---|---|---|---|
| 33 | $C_{11}H_{23}O-$ | 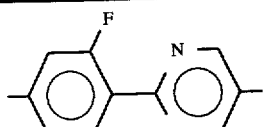 | $-CH_2CH_2-$ | 3 | H | Same as in Example 1 |
| 34 | $C_{10}H_{21}O-$ | 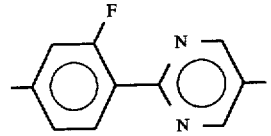 | $-CH_2CH_2-$ | 5 | F | Same as in Example 1 |
| 35 | $C_{12}H_{25}O-$ | 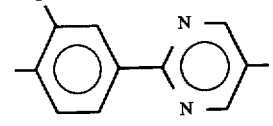 | $-CH_2CH_2-$ | 3 | H | Same as in Example 1 |
| 36 | $C_{10}H_{21}O-$ | 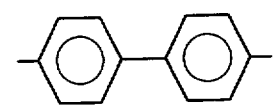 | $-CH_2CH_2-$ | 3 | H | Same as in Example 1 |

TABLE 5

| Example No. | Alcohol derivative (2) $R^1-(O)_m-$ | $-A^1-(A^2)_p-(A^3)_q-$ | X | n | W | Fluorinating agent & Reaction condition |
|---|---|---|---|---|---|---|
| 37 | $C_{10}H_{21}-$ | 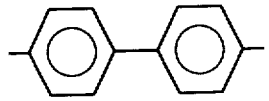 | $-CH_2CH_2-$ | 6 | H | Same as in Example 1 |
| 38 | $C_{10}H_{21}O-$ | 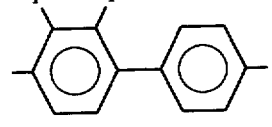 | $-CH_2CH_2-$ | 4 | H | Same as in Example 1 |
| 39 | $C_9H_{19}O-$ | 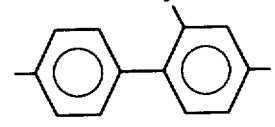 | $-CH_2CH_2-$ | 3 | H | Same as in Example 1 |
| 40 | $C_8H_{17}O-$ | 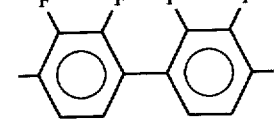 | $-CH_2CH_2-$ | 3 | H | Same as in Example 1 |
| 41 | $C_8H_{17}O-$ | 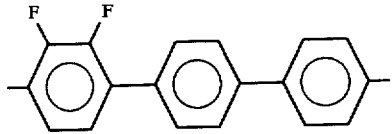 | $-CH_2CH_2-$ | 3 | H | Same as in Example 1 |

TABLE 5-continued

| Example No. | Alcohol derivative (2) | | X | n | W | Fluorinating agent & Reaction condition |
|---|---|---|---|---|---|---|
| | $R^1-(O)_m-$ | $-A^1-(A^2)_p-(A^3)_q-$ | | | | |
| 42 | $C_{10}H_{21}O-$ | 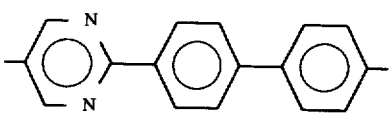 | $-CH_2CH_2-$ | 3 | H | Same as in Example 1 |

TABLE 6

| Example No. | Alcohol derivative (2) | | X | n | W | Fluorinating agent & Reaction condition |
|---|---|---|---|---|---|---|
| | $R^1-(O)_m-$ | $-A^1-(A^2)_p-(A^3)_q-$ | | | | |
| 43 | $C_{12}H_{25}O-$ | 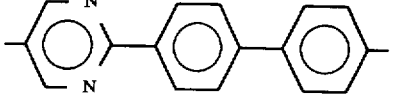 | $-CH_2CH_2-$ | 3 | H | Same as in Example 1 |
| 44 | $C_6H_{13}-$ | 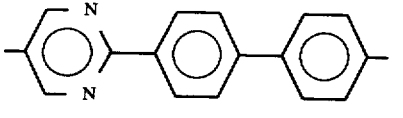 | $-CH_2CH_2-$ | 6 | H | Same as in Example 1 |
| 45 | $C_{10}H_{21}O-$ | 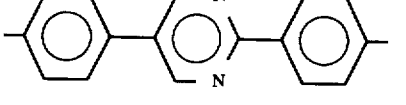 | $-CH_2CH_2-$ | 3 | H | Same as in Example 1 |
| 46 | $C_{10}H_{21}O-$ | 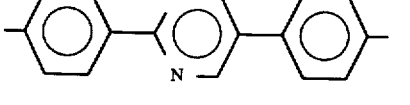 | $-CH_2CH_2-$ | 3 | H | Same as in Example 1 |
| 47 | $C_6H_{13}O-$ | 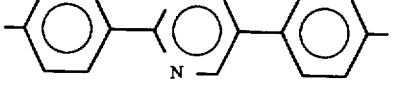 | $-CH_2CH_2-$ | 6 | H | Same as in Example 1 |
| 48 | $C_7H_{15}O-$ | 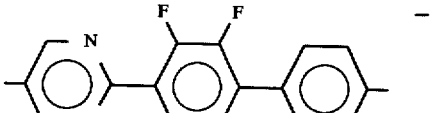 | $-CH_2CH_2-$ | 3 | H | Same as in Example 1 |

TABLE 7

| Example No. | Alcohol derivative (2) $R^1-(O)_m-$ | $-A^1-(A^2)_p-(A^3)_q-$ | X | n | W | Fluorinating agent & Reaction condition |
|---|---|---|---|---|---|---|
| 49 | $C_6H_{13}O-$ | 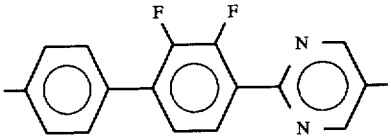 | $-CH_2CH_2-$ | 3 | H | Same as in Example 1 |
| 50 | $C_8H_{17}-$ | 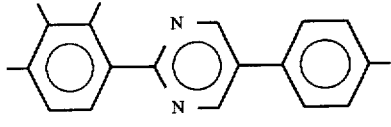 | $-CH_2CH_2-$ | 3 | H | Same as in Example 1 |
| 51 | $C_9H_{19}O-$ | 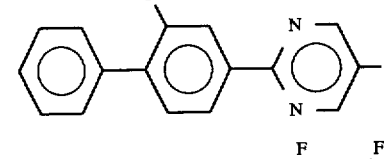 | $-CH_2CH_2-$ | 3 | H | Same as in Example 1 |
| 52 | $C_{10}H_{21}O-$ | 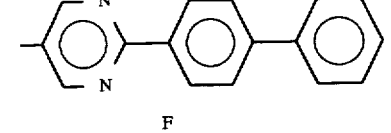 | $-CH_2CH_2-$ | 3 | H | Same as in Example 1 |
| 53 | $C_{10}H_{21}O-$ | 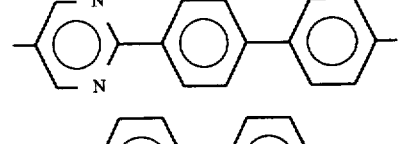 | $-CH_2CH_2-$ | 3 | H | Same as in Example 1 |
| 54 | $C_{10}H_{21}O-$ | 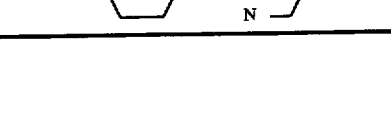 | $-CH_2CH_2-$ | 2 | H | Same as in Example 1 |

TABLE 8

| Example No. | Alcohol derivative (2) $R^1-(O)_m-$ | $-A^1-(A^2)_p-(A^3)_q-$ | X | n | W | Fluorinating agent & Reaction condition |
|---|---|---|---|---|---|---|
| 55 | $C_{10}H_{21}-$ | 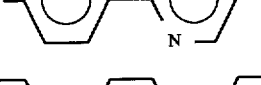 | $-CH_2CH_2-$ | 5 | F | Same as in Example 1 |
| 56 | $C_{10}H_{21}O-$ | 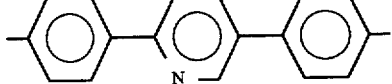 | $-CH_2CH_2-$ | 3 | H | Same as in Example 1 |
| 57 | $C_{10}H_{21}O-$ | 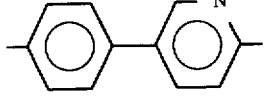 | $-CH_2CH_2-$ | 2 | H | Same as in Example 1 |

TABLE 8-continued

| Example No. | Alcohol derivative (2) $R^1-(O)_m-$ | $-A^1-(A^2)_p-(A^3)_q-$ | X | n | W | Fluorinating agent & Reaction condition |
|---|---|---|---|---|---|---|
| 58 | $C_{10}H_{21}O-$ | 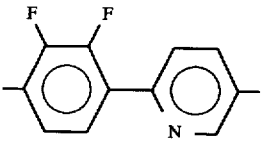 | $-CH_2CH_2-$ | 2 | H | Same as in Example 1 |
| 59 | $C_8H_{17}O-$ | 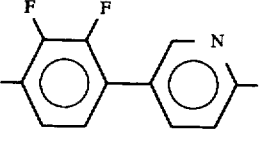 | $-CH_2CH_2-$ | 2 | H | Same as in Example 1 |
| 60 | $C_{12}H_{25}O-$ | 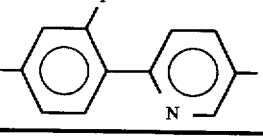 | $-CH_2CH_2-$ | 2 | H | Same as in Example 1 |

TABLE 9

| Example No. | Alcohol derivative (2) $R^1-(O)_m-$ | $-A^1-(A^2)_p-(A^3)_q-$ | X | n | W | Fluorinating agent & Reaction condition |
|---|---|---|---|---|---|---|
| 61 | $C_{10}H_{21}O-$ | 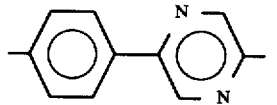 | $-CH_2CH_2-$ | 2 | H | Same as in Example 1 |
| 62 | $C_{10}H_{21}-$ | 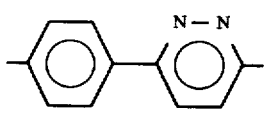 | $-CH_2CH_2-$ | 2 | H | Same as in Example 1 |
| 63 | $C_{10}H_{21}O-$ | 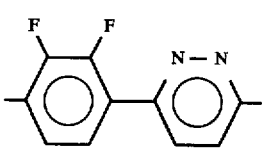 | $-CH_2CH_2-$ | 2 | H | Same as in Example 1 |
| 64 | $C_{10}H_{21}O-$ | 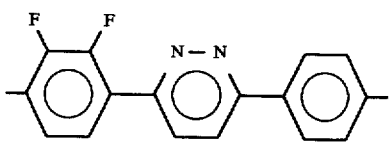 | $-CH_2CH_2-$ | 3 | H | Same as in Example 1 |
| 65 | $C_{12}H_{25}O-$ | 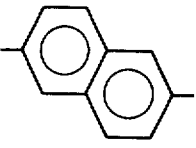 | $-CH_2CH_2-$ | 3 | H | Same as in Example 1 |

TABLE 9-continued

| Example No. | Alcohol derivative (2) R¹—(O)$_m$— | —A¹—(A²)$_p$—(A³)$_q$— | X | n | W | Fluorinating agent & Reaction condition |
|---|---|---|---|---|---|---|
| 66 | $C_{10}H_{21}O$— | 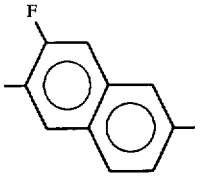 | —$CH_2CH_2$— | 3 | H | Same as in Example 1 |

TABLE 10

| Example No. | Alcohol derivative (2) R¹—(O)$_m$— | —A¹—(A²)$_p$—(A³)$_q$— | X | n | W | Fluorinating agent & Reaction condition |
|---|---|---|---|---|---|---|
| 67 | $C_{10}H_{21}O$— | 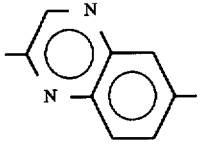 | —$CH_2CH_2$— | 3 | H | Same as in Example 1 |
| 68 | $C_{10}H_{21}O$— | 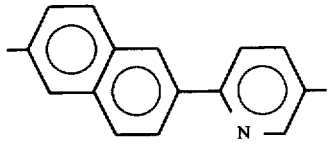 | —$CH_2CH_2$— | 3 | H | Same as in Example 1 |
| 69 | $C_{10}H_{21}O$— | 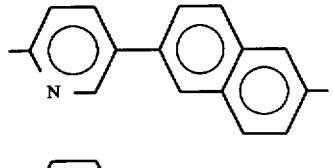 | —$CH_2CH_2$— | 3 | H | Same as in Example 1 |
| 70 | $C_{10}H_{21}O$— | 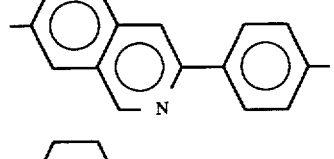 | —$CH_2CH_2$— | 3 | H | Same as in Example 1 |
| 71 | $C_{10}H_{21}O$— | 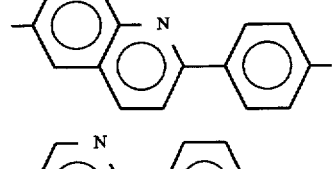 | —$CH_2CH_2$— | 3 | H | Same as in Example 1 |
| 72 | $C_{10}H_{21}O$— | 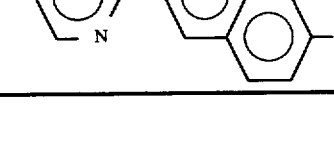 | —$CH_2CH_2$— | 3 | H | Same as in Example 1 |

TABLE 11

| Example No. | Alcohol derivative (2) $R^1-(O)_m-$ | $-A^1-(A^2)_p-(A^3)_q-$ | X | n | W | Fluorinating agent & Reaction condition |
|---|---|---|---|---|---|---|
| 73 | $C_{10}H_{21}O-$ | 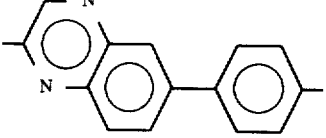 | $-CH_2CH_2-$ | 3 | H | Same as in Example 1 |
| 74 | $C_{10}H_{21}O-$ | 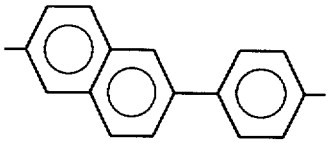 | $-CH_2CH_2-$ | 3 | H | Same as in Example 1 |
| 75 | $C_9H_{19}O-$ | 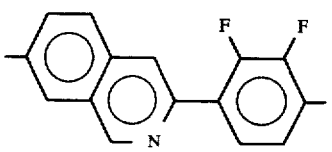 | $-CH_2CH_2-$ | 3 | H | Same as in Example 1 |
| 76 | $C_8H_{17}O-$ | 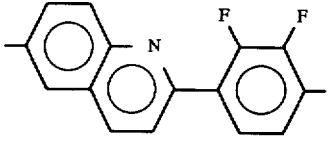 | $-CH_2CH_2-$ | 3 | H | Same as in Example 1 |
| 77 | $C_{10}H_{21}O-$ | 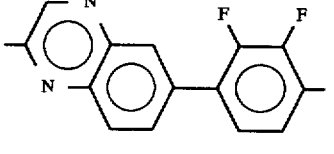 | $-CH_2CH_2-$ | 3 | H | Same as in Example 1 |
| 78 | $C_6H_{13}O-$ | 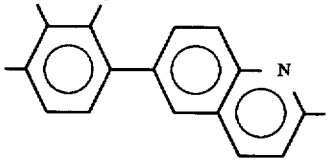 | $-CH_2CH_2-$ | 3 | H | Same as in Example 1 |

TABLE 12

| Example No. | Alcohol derivative (2) $R^1-(O)_m-$ | $-A^1-(A^2)_p-(A^3)_q-$ | X | n | W | Fluorinating agent & Reaction condition |
|---|---|---|---|---|---|---|
| 79 | $C_{10}H_{21}O-$ | 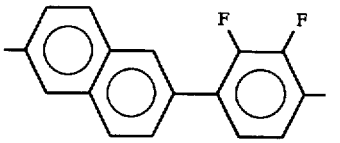 | $-CH_2CH_2-$ | 3 | H | Same as in Example 1 |

TABLE 12-continued

| Example No. | Alcohol derivative (2) | | | | Fluorinating agent & Reaction |
|---|---|---|---|---|---|
| | $R^1-(O)_m-$ | $-A^1-(A^2)_p-(A^3)_q-$ | X | n | W condition |
| 80 | $C_8H_{17}O-$ | (difluorophenyl-phenyl-phenyl) | $-CH_2CH_2-$ | 3 | H Same as in Example 1 |

REFERENCE EXAMPLE 1

In a reactor equipped with a stirrer and a thermometer, 5-decyloxy-2-(4-bromophenyl)pyrimidine (25 g), optically active 6-hydroxy-1-heptyne (8.58 g), dichlorobis(triphenylphosphine)palladium (0.1 g), copper iodide (0.1 g), triphenylphosphine (0.52 g) and triethylamine (200 ml) are charged and heated up to 90° C. to carry out a reaction for 10 hours. After evaporating triethylamine off under reduced pressure, toluene and 10% hydrochloric acid are added to the residue for extraction, and the organic layer is washed with water and evaporated under reduced pressure. A resulting residue is purified by silica gel column chromatography (eluent: hexane-ethyl acetate) to obtain (−)-5-decyloxy-2-|4-(6-hydroxyheptynyl)phenyl|-pyrimidine (23.4 g). $[\alpha]_D^{20} = -3.3°$ (c=1.035, $CHCl_3$).

REFERENCE EXAMPLE 2

In a reactor equipped with a stirrer and a thermometer, 5-decyloxy-2-(4-bromophenyl)pyrimidine (13.98 g), dry tetrahydrofuran (THF) (30 ml), tetrakis(triphenylphosphine)palladium (0.11 g) and sodium hydroxide (1.2 g) are charged. To the mixture, a solution of a reaction product of 6-hydroxy-1-heptyne and catechol borane (5 g) dissolved in THF (12 ml) is dropwise added, followed by heating up to a refluxing temperatur. After reacting for 4 hours, the reaction mixture is cooled to room temperature. To the mixture, toluene and water are added for extraction, and the organic layer is washed with water, dried over anhydrous magnesium sulfate and evaporated under reduced pressure. A resulting residue is purified by silica gel column chromatography (eluent: toluene-ethyl acetate) to obtain (−)-5-decyloxy-2-|4-(6-hydroxyheptenyl)phenyl|pyrimidine (7.99 g).

REFERENCE EXAMPLE 3

In a reactor equipped with a stirrer and a thermometer, (−)-5-decyloxy-2-|4-(6-hydroxyheptynyl)phenyl| pyrimidine (4.0 g), 5% Pd/C (0.5 g) and THF (50 ml) are charged, and the mixture is reacted at room temperature for 17 hours in a hydrogen atmosphere under ordinary pressure. After filtrating the catalyst off, the reaction mixture is evaporated under reduced pressure. A resulting residue is purified by silica gel column chromatography (eluent: toluene-ethyl acetate) to obtain (−)-5-decyloxy-2-|4-(6-hydroxyheptyl)phenyl|pyrimidine (4.11 g). $[\alpha]_D = -2.8°$ (c=1.055, $CHCl_3$).

REFERENCE EXAMPLE 4

(1) In a reactor equipped with a stirrer and a thermometer, 2-(4-bromophenyl)-5-benzyloxypyrimidine, 6-tetrahydropyranyloxy-1-heptyne, dichlorobis(triphenylphosphine)palladium, copper iodide, triphenylphosophine and triethylamine are charged and heated up to 90° C. to carry out a reaction for 8 hours. After extraction with toluene and washing with water, the mixture is evaporated under reduced pressure. A resulting residue is purified by silica gel column chromatography to obtain 5-benzyloxy-2-|4-(6-tetrahydropyranyloxy-1-heptynyl)phenyl| pyrimidine.

(2) In a reactor equipped with a stirrer and a thermometer, 5-benzyloxy-2-|4-(6-tetrahydropyranyloxy-1-heptynyl) phenyl|pyrimidine, 5% Pd/C and THF are charged. After replacing an internal atmosphere of the reactor by hydrogen gas under atmospheric pressure, the mixture is reacted at room temperature for 10 hours in a hydrogen atmosphere under ordinary pressure. After filtrating the catalyst off, the reaction mixture is evaporated under reduced pressure. A resulting residue is purified by silica gel column chromatography to obtain 5-hydroxy-2-|4-(6-tetrahydropyranyloxy1-heptyl)phenyl|pyrimidine.

(3) In a reactor equipped with a stirrer and a thermometer, 5-hydroxy-2-|4-(6-tetrahydropyranyloxy-1-heptyl)phenyl| pyrimidine, pyridine, dichloromethane and a catalytic amount of 4-pyrrolidinopyridine are charged, and the mixture is cooled to 0° C. Then, to the cooled mixture, anhydrous trifluoromethanesulfonic acid is dropwise added. After carrying out the reaction at 0° C. for 2 hours, the reaction mixture is poured in iced water, and the organic layer is washed with water several times. After evaporating the organic layer under reduced pressure, a resulting residue is purified by silica gel column chromatography to obtain 5-trifluoromethylsulfoxyl-2-|4-(6-tetrahydropyranyloxy-1-heptyl)phenyl|pyrimidine.

(4) In a reactor equipped with a stirrer and a thermometer, 5-trifluoromethylsulfoxyl-2-|4-(6-tetrahydropyranyloxy-1-heptyl)phenyl|pyrimidine, 1-E-nonenylboric acid, sodium carbonate, tetrakis(triphenylphosphine)palladium, ethanol, toluene and water are charged and heated up to a refluxing temperature. After carrying out the reaction at the refluxing temperature for 5 hours, the reaction mixture is cooled to room temperature. The organic layer is washed with a 5% aqueous solution of sodium hydroxide and then with water. After evaporating the organic layer under reduced pressure, a resulting residue is purified by silica gel column chromatography to obtain 5-nonenyl-2-|4-(6-tetrahydropyranyloxy-1-heptyl)phenyl|-pyrimidine (5) In a reactor equipped with a stirrer and a thermometer, 5-nonenyl-2-|4-(6-tetrahydropyranyloxy-1-heptyl)phenyl|-pyrimidine, p-toluenesulfonic acid and methanol are charged and reacted at room temperature for 2 hours. Then, the reaction mixture is extracted with toluene and the extract is washed with water and evaporated under reduced pressure. A resulting residue is purified by silica gel column chromatography to obtain 5-nonenyl-2-[4-(6-hydroxy-1-heptyl)phenyl]pyrimidine

What is claimed is:

1. A fluorine-containing optically active compound represented by the formula (1):

$$R^1-(O)_m-A^1-(A^2)_p-(A^3)_q-X-(CH_2)_n-\overset{\overset{\displaystyle C(W)_3}{|}}{C^*H}-F \quad (1)$$

wherein $R^1$ is a saturated or unsaturated $C_3-C_{20}$ alkyl group or a saturated or unsaturated $C_3-C_{20}$ alkoxyalkyl group; $A^1$, $A^2$ and $A^3$ independently represent one of the following groups:

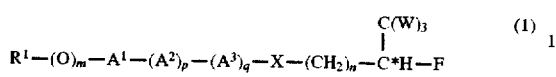

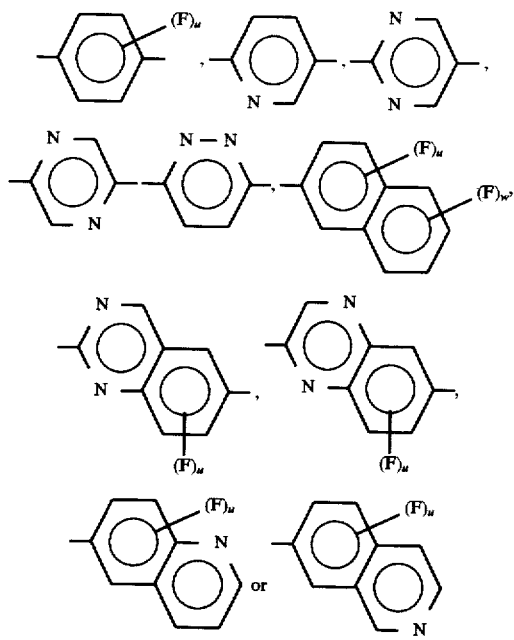

provided that, when $A^1$ is a condensed ring group, a sum of p and q is 0 or 1 and $A^2$ and $A^3$ are both monocyclic groups, or when $A^1$ is a monocyclic group, a sum of p and q is 1 or 2 with the proviso that when the sum of p and q is 2, $A^2$ and $A^3$ are both monocyclic groups; X is —CH$_2$CH$_2$—, —CH=CH— or —C≡C—; W is a fluorine atom or a hydrogen atom; n is an integer of 1 to 10; m, p and q are each 0 or 1; u and w are each an integer of 0 to 3; and * indicates an asymmetric carbon atom; and with the further proviso that $A^3$ is not

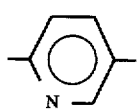

when X is —CH$_2$CH$_2$—, $A^1$ is a monocyclic group, and q is 1, or that $A^2$ is not

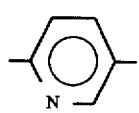

when X is —CH$_2$CH$_2$—, $A^1$ is a monocyclic group, and q is 0.

2. The fluorine-containing optically active compound according to claim 1, wherein p is 1 and $A^3$ is one of

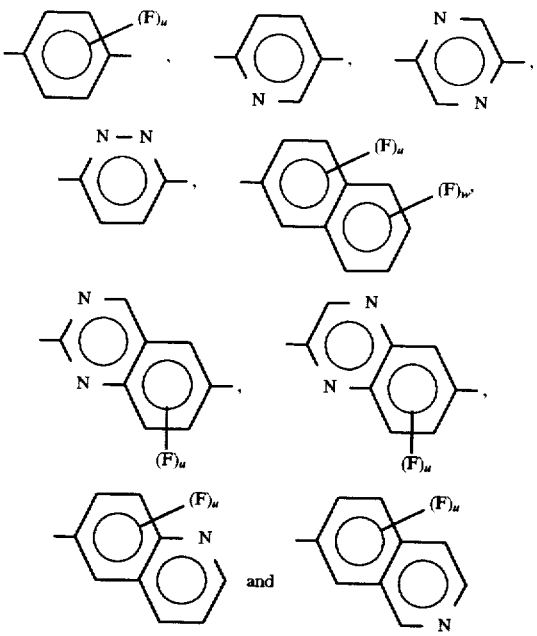

wherein u and w are the same as defined in claim 1.

3. The fluorine-containing optically active compound according to claim 1, wherein $A^1$, $A^2$ and $A^3$ are each

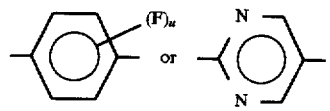

4. The fluorine-containing optically active compound according to claim 1, wherein $R^1$ is an alkyl group or an alkenyl group.

5. The fluorine-containing optically active compound according to claim 1, wherein $R^1$ is an alkoxyalkyl group, an alkenyloxyalkyl group, an alkoxyalkenyl group, or an alkenyloxyalkenyl group.

6. The fluorine-containing optically active compound according to claim 3, wherein p is 1 and q is 0.

7. The fluorine-containing optically active compound according to any one of claims 1 to 6, wherein W is a hydrogen atom and X is —CH$_2$CH$_2$—.

8. The fluorine-containing optically active compound according to claim 7, wherein
one of $A^1$ and $A^2$ is

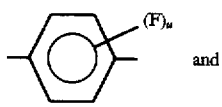

the other of $A^1$ and $A^2$ is

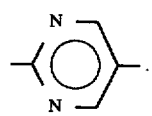

9. The fluorine-containing optically active compound according to claim 8, which is a compound of the formula:

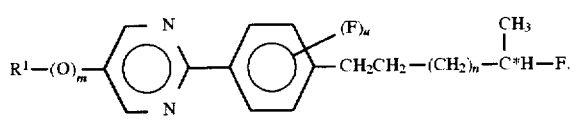

10. The fluorine-containing optically active compound according to claim 8, which is a compound of the formula:

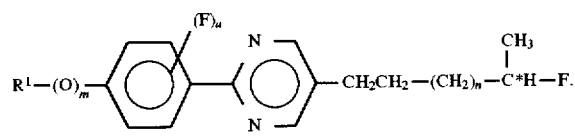

11. A process for preparing a fluorine-containing compound of the formula (1) as claimed in claim 1, comprising fluorinating an alcohol derivative of the formula:

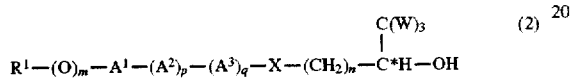

wherein $R^1$, $A^1$, $A^2$, $A^3$, X, W, m, n, p and q are the same as defined in claim 1, with a fluorinating agent.

12. A liquid crystal mixture comprising a fluorine-containing optically active compound of the formula (1) as claimed in claim 1.

13. A liquid crystal display element comprising a fluorine-containing optically active compound of the formula (1) as claimed in claim 1.

14. The fluorine-containing optically active compound according to claim 1, which is 5-decyloxy-2-|4-(6-fluoroheptyl)phenyl|pyrimidine.

15. A fluorine-containing optically active compound represented by the formula (1):

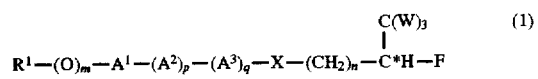

wherein $R^1$ is a saturated or unsaturated $C_3$–$C_{20}$ alkyl group or a saturated or unsaturated $C_3$–$C_{20}$ alkoxyalkyl group; $A^1$, $A^2$ and $A^3$ independently represent one of the following groups:

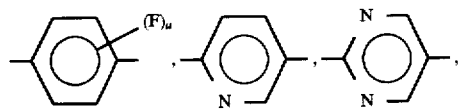

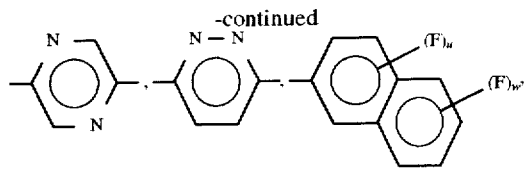

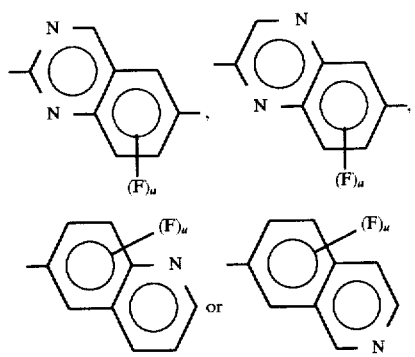

provided that, when $A^1$ is a condensed ring group, a sum of p and q is 0 or 1 and $A^2$ and $A^3$ are both monocyclic groups, or when $A^1$ is a monocyclic group, a sum of p and q is 1 or 2 with the proviso that when the sum of p and q is 2, $A^2$ and $A^3$ are both monocyclic groups; X is —$CH_2CH_2$—, —CH=CH— or —ClC—; W is a fluorine atom or a hydrogen atom; n is an integer of 1 to 10; m, p and q are each 0 or 1; u and w are each an integer of 0 to 3; and * indicates an asymmetric carbon atom; and with the further proviso that $A^3$ is not

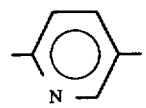

when $A^1$ is a monocyclic group and q is 1, or that $A^2$ is not

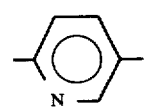

when $A^1$ is a monocyclic group and q is 0.

\* \* \* \* \*